United States Patent [19]
Liao et al.

[11] Patent Number: 6,153,392
[45] Date of Patent: Nov. 28, 2000

[54] DEVICES AND METHODS COMPRISING AN HBCAG FROM HEPATITIS B VIRUS

[75] Inventors: Jaw-Ching Liao, Taipei; Cheng-Nan Wang, Tapei, both of Taiwan

[73] Assignee: Bionova Corporation, San Francisco, Calif.

[21] Appl. No.: 09/115,350

[22] Filed: Jul. 14, 1998

Related U.S. Application Data

[60] Provisional application No. 60/054,194, Jul. 30, 1997.

[51] Int. Cl.[7] .......................... G01N 33/53; G01N 33/537; G01N 33/543; C12Q 1/00; C12Q 1/70
[52] U.S. Cl. .................................... 435/7.1; 435/5; 435/4; 435/7.92; 536/23.72
[58] Field of Search ........................... 435/5, 4, 7.1, 7.92; 536/23.72

[56] References Cited

U.S. PATENT DOCUMENTS 5,376,557  12/1994  Schmitt .................................... 436/513

FOREIGN PATENT DOCUMENTS

| | | |
|---|---|---|
| 318 216 A1 | 5/1989 | European Pat. Off. . |
| 341 439 A1 | 11/1989 | European Pat. Off. . |
| 366 092 A2 | 5/1990 | European Pat. Off. . |
| 870 830 A2 | 10/1998 | European Pat. Off. . |
| WO 94/25874 | 11/1994 | WIPO . |
| WO 96/38474 | 12/1996 | WIPO . |

OTHER PUBLICATIONS

Yamaki et al.; Circular dichroism and biochemical properties of the hepatitis B viru core antigen; Biocemica of Biophysica Acta; vol. 706; pp. 165–173, 1982.

*Primary Examiner*—Jeffrey Stucker
*Assistant Examiner*—Brett Nelson
*Attorney, Agent, or Firm*—Seed Intellectual Property Law Group PLLC

[57] ABSTRACT

A complex comprised of the HBcAg and an albumin or an unprocessed structural protein from a positive stranded RNA virus. Pursuant to such complexing, the antigenicity of the HBcAg is enhanced when compared to HBcAg alone, in terms of both or either affinity or specificity. This complexed HBcAg can be recognized by the immune system, which produces antibodies that have a high specificity and affinity for the complexed HBcAg, although such antibodies typically do also bind the uncomplexed antigen to a lower specificity and affinity. Also, methods and devices using the same.

24 Claims, 1 Drawing Sheet

DEVICES AND METHODS COMPRISING AN HBCAG FROM HEPATITIS B VIRUS

The present application claims priority from U.S. Provisional Application Ser. No. 60/054,194, filed Jul. 30, 1997, which application is incorporated herein by reference in its entirety.

TECHNICAL FIELD

The present invention relates generally to the antigen HBcAg from hepatitis B virus (HBV) complexed to a second protein, antibodies against such a complexed HBcAg, and to methods and compositions for the detection of such a complexed HBcAg. The methods and compositions are also suitable for the elicitation of an immune response in an animal, and for the vaccination of an animal, against the complexed HBcAg.

BACKGROUND OF THE INVENTION

Hepatitis B virus (HBV) is a double stranded DNA virus that may be carried by as much as 20% or more of the apparently healthy population in certain parts of the world, such as Africa, Asia and the Pacific Region. Principles and Practice of Clinical Virology, 3rd Edition, Chapter 2: Hepatitis Viruses, pp. 162–180. The reservoir of carriers worldwide is estimated at a number over 300 million. HBV was originally thought to be spread exclusively by blood and blood products, although it now appears that HBV can also be transmitted by intimate contact, such as sexual contact, and other routes may also be possible. Thus, transmission of infection may result from accidental inoculation of minute amounts of blood, or fluid contaminated with blood, during medical, surgical and dental procedures; immunization with inadequately sterilized syringes and needles; intravenous or percutaneous drug abuse; tatooing; car, nose and other piercing; acupuncture; laboratory accidents; and, accidental inoculation with razors and similar objects that have been contaminated with blood. Id.

HBV comprises at least three morphologically distinct forms, an about 22 nm spherical particle, a tubular form of roughly the same diameter that is composed of the virus surface protein, and a 42 nm double-shelled virion. The core or nucleocapsid of HBV comprises the genome surrounded by a second protein, hepatitis B core antigen (HBcAg; also known as p22). Other HBV antigens include the HBsAg and HBeAg. Id.; Zuckerman, A. J., Human Viral Hepatitis (North-Holland/American Elsevier, Amsterdam, 1975).

The genomes of a variety of isolates of HBV have been cloned and the complete nucleotide sequence thereof determined. Although there is some variation in sequence (up to about 12% of nucleotides) between these isolates, the genetic organization and other essential features are conserved. The genome is around 3200 base pairs in length and analysis of the protein coding potential reveals four conserved ORFs. The four ORFs are located on the same DNA strand and the strands of the genome have accordingly been designated the plus (incomplete strand) and minus (complete strand) as shown in FIG. 1 hereto.

The core protein (HBcAg) is the major component of the nucleocapsid and includes an arginine-rich domain in the carboxyl terminus that presumably interacts with the viral nucleic acid. Antibodies against this protein (anti-HBcAg) are important in diagnosis because anti-HBcAg tends to maintain a relatively significant presence in the blood over time. Principles and Practice of Clinical Virology, 3rd Edition, Chapter 2: Hepatitis Viruses, p. 170.

Assays for the diagnosis of the potential presence of HBV in a patient, as indicated by the presence of the HBcAg, are known in the art. However, it is believed that such assays do not detect very small quantities of HBcAg in a sample, and therefore assays having increased sensitivity for HBcAg are needed to enhance the detection of HBcAg, and therefore HBV. Such a need is accentuated due to the need to inhibit transmission of HBV via the blood, for example due to blood transfusions and other blood-related activities.

Thus, there has gone unmet a need for products and methods capable of highly specific, highly sensitive detection of HBV. There has also gone unmet a need for products and methods capable of eliciting, or enhancing the elicitation of, an immune response to HBV, especially an immunoprotective immune response to HBV. The present invention utilizes properties of the HBcAg of HBV to provide these advantages, as well as other related advantages.

SUMMARY OF THE INVENTION

The present invention is directed to the use of the HBcAg of HBV as an active component of the immune response. The HBcAg interacts with certain other enhancing proteins, preferably an albumin and/or an unprocessed structural protein from a positive stranded RNA virus, to provide a complex comprised of the HBcAg and the albumin or unprocessed structural protein from the positive stranded RNA virus. Pursuant to such complexing, the HBcAg is believed to undergo conformational changes that enhance the antigenicity of the HBcAg when compared to HBcAg alone in terms of both or either affinity or specificity. This complexed HBcAg can be recognized by the immune system, which produces antibodies that have a higher specificity and affinity for the HBcAg than is found for antibodies produced using uncomplexed HBcAg.

The discovery of these advantages found with a complexed HBcAg permits the design of assays, methods and compositions that are directed toward the detection of antibodies in a sample against the HBcAg (and therefore HBV) using the complexed HBcAg, and the making and use of antibodies made against such a complexed HBcAg. Such discovery also permits the design of compositions and methods for the induction of an immune response in an animal, including an immunoprotective immune response.

In addition, it has been found that the complexed HBcAg can be used in an assay or immuno-inducing composition with one or more core-like antigen-adjacent proteins from one or more respective positive stranded RNA viruses (which core-like antigen-adjacent proteins are preferably complexed with a second protein (other than HBcAg) that causes an synergistic effect in the core-like antigen-adjacent protein that is similar to the synergistic effect described herein for the HBcAg). Such combining of complexed HBcAgs and one or more complexed core-like antigen-adjacent proteins provides assays able to detect more than one target virus (HBV and one or more selected viruses) and multi-valent vaccines.

Accordingly, in one aspect the present invention provides assays for the detection of an antibody against an HBcAg in a sample, comprising: (a) providing an HBcAg complexed with a protein selected from the group consisting of a serum albumin and a core-like antigen-adjacent protein of a positive stranded RNA virus, to provide an HBcAg-protein complex; (b) contacting the HBcAg-protein complex with the sample under conditions suitable and for a time sufficient for the HBcAg-protein complex to bind to one or more antibodies against HBcAg present in the sample, to provide an antibody-bound complex; and (c) detecting the antibody-bound complex, and therefrom determining whether the sample contains an antibody against HBcAg. In preferred embodiments for this and other detection aspects of the invention, the assay further comprises the step of binding the HBcAg-protein complex, or other detection substrate, such as an antibody, to a solid substrate.

The present invention also provides assays for the detection of an antibody against an HBcAg or an independent core-like antigen-adjacent protein of a positive stranded RNA virus in a sample. The "independent" core-like antigen-adjacent protein of a positive stranded RNA virus can be of the same species or strain of positive stranded RNA virus as the core-like antigen-adjacent protein that is complexed to the HBcAg, or it may be a different core-like antigen-adjacent protein from a different positive stranded RNA virus, but the independent core-like antigen-adjacent protein is separate from the core-like antigen-adjacent protein complexed to the HBcAg. Preferably the independent core-like antigen-adjacent protein is also complexed to a protein, as discussed below, that enhances the antigenicity of the independent core-like antigen-adjacent protein, such protein is typically not an HBcAg.

An assay comprising the HBcAg and the independent core-like antigen-adjacent protein comprises: (a) providing an HBcAg complexed with a protein selected from the group consisting of a serum albumin and a core-like antigen-adjacent protein of a positive stranded RNA virus, to provide an HBcAg-protein complex, and providing an independent core-like antigen-adjacent protein of a positive stranded RNA virus complexed to a protein, to provide an independent core-like antigen-adjacent protein complex; (b) contacting the HBcAg-protein complex and the independent core-like antigen-adjacent protein complex with the sample under conditions suitable and for a time sufficient for the HBcAg-protein complex and the independent core-like antigen-adjacent protein complex to bind to one or more antibodies against the HBcAg or the independent core-like antigen-adjacent protein present in the sample, thereby providing one or more antibody-bound complexes; and (c) detecting the one or more antibody-bound complexes, and therefrom determining whether the sample contains an antibody against HBcAg or the independent core-like antigen-adjacent protein. Preferably, the step of detecting allows the differentiation between different antibody-bound complexes. Also preferably, the assay comprises at least two or three independent core-like antigen-adjacent proteins, at least two or three, respectively, of which are from different positive-stranded RNA viruses, and wherein the step of contacting is performed under conditions suitable and for a time sufficient for each of the HBcAg and the at least two or three independent core-like antigen-adjacent proteins to bind to one or more antibodies specific therefor, thereby providing one or more antibody-bound complexes.

In preferred embodiments for the assays and other aspects of the invention discussed herein, the positive stranded RNA virus is selected from the group consisting of Togaviridae, Coronaviridae, Retroviridae, Picornaviridae, Caliciviridae and Flaviviridae, further preferably from the group consisting of hepatitis C virus (HCV), Human Immunodeficiency virus (HIV) and Human T-cell Leukemia virus (HTLV). Also preferably, the serum albumin is selected from the group consisting of human serum albumin, α-fetoprotein, bovine serum albumin, fetal bovine serum albumin, new born bovine serum albumin and mouse serum albumin. In other preferred embodiments, the sample is an unpurified sample, further preferably a human being, although the sample can also be from a non-human animal. The sample can be a blood sample, and in one preferred embodiment the serum albumin is selected from the same species as the sample.

Preferred assays for use with the present invention include countercurrent immuno-electrophoresis (CIEP) assay, a radioimmunoassay, a western blot assay, a radioimmunoprecipitation, an enzyme-linked immunosorbent assay (ELISA), a dot blot assay, an inhibition or competition assay, a sandwich assay, an immunostick (dipstick) assay, a simultaneous assay, an immunochromatographic assay, an immunofiltration assay, a latex bead agglutination assay, an immunofluorescent assay, a biosensor assay, and a low-light detection assay.

In another aspect, the present invention provides methods of producing an antibody specific for an HBcAg, the methods comprising administering to an animal the HBcAg complexed with a protein selected from the group consisting of a serum albumin and a core-like antigen-adjacent protein of a positive stranded RNA virus, to provide an HBcAg-protein complex, the administering occurring under conditions suitable and for a time sufficient to induce the production in the animal of antibodies against the HBcAg; and isolating the antibodies to the complexed HBcAg.

The antibodies can be used in assay for the detection of an HBcAg in a sample, for example comprising contacting the sample with the antibody under conditions suitable and for a time sufficient for the antibody to bind the HBcAg, to provide a bound antibody; and then detecting the bound antibody, and therefrom determining whether the sample contains the HBcAg.

The present invention also provides methods of producing an assay to detect an antibody against an HBcAg comprising contacting the HBcAg with a protein selected from the group consisting of a serum albumin and a core-like antigen-adjacent protein of a positive stranded RNA virus, to provide an HBcAg-protein complex, and then binding the complex to a solid substrate.

In preferred embodiments, the HBcAg is contacted with the serum albumin in a TNSCN buffer.

In still other aspects, the present invention provides compositions capable of binding to an antibody against an HBcAg, the composition comprising an isolated HBcAg complexed with a protein selected from the group consisting of a serum albumin and a core-like antigen-adjacent protein of a positive stranded RNA virus, to provide an isolated HBcAg-protein complex, preferably bound to a solid substrate.

In yet another aspect, the present invention provides compositions comprising two or more different antigens capable of binding to an antibody against an HBcAg or an antibody against an independent core-like antigen of a positive stranded RNA virus, the compositions comprising (a) an isolated HBcAg complexed with a protein selected from the group consisting of a serum albumin and a core-like antigen-adjacent protein of a positive stranded RNA virus and (b) an independent core-like antigen-adjacent protein of a positive stranded RNA virus complexed to a protein, to provide an isolated HBcAg-protein complex and an independent core-like antigen-adjacent protein complex. Preferably, the compositions comprise at least two or three of the independent core-like antigen-adjacent proteins, at least two or three of which are from different positive-stranded RNA viruses.

In preferred embodiments, the core-like antigen-adjacent protein used in the present invention is produced by a suitable prokaryotic host cell or by a eukaryotic host cell that is unable to process the core-like antigen-adjacent protein.

In still yet a further aspect, the present invention provides compositions capable of binding to an HBcAg, the composition comprising an antibody produced against an HBcAg-protein complex comprised of the HBcAg complexed with a protein selected from the group consisting of a serum albumin and a core-like antigen-adjacent protein of a positive stranded RNA virus, the antibody bound to a solid substrate.

In another aspect, the present invention provides compositions capable of eliciting an immune response in an animal comprising an HBcAg-protein complex comprised of the HBcAg complexed with a protein selected from the group consisting of a serum albumin and a core-like antigen-adjacent protein of a positive stranded RNA virus, in combination with a pharmaceutically acceptable carrier or diluent. Preferably, the animal is a human being.

The present invention also provides methods of making compositions able to induce an immune response to an HBcAg, comprising complexing an HBcAg with a protein selected from the group consisting of a serum albumin and a core-like antigen-adjacent protein of a positive stranded RNA virus, to provide an HBcAg-protein complex, and combining the complex with a pharmaceutically acceptable carrier or diluent. The present invention also provides methods of using such compositions to induce an immune response in the animal.

In still yet another aspect, the present invention provides kits for the detection of an HBcAg, comprising an HBcAg-protein complex comprised of the HBcAg complexed with a protein selected from the group consisting of a serum albumin and a core-like antigen-adjacent protein of a positive stranded RNA virus, and one or both of a reagent or a device for detecting the complex or an antibody bound to the complex. Preferably, the kits further comprise one or more independent core-like antigens of a positive stranded RNA virus complexed to a protein.

The present invention further provides kits for the detection of an HBcAg, comprising an antibody produced according to the methods described herein and one or both of a reagent or a device for detecting the antibody.

These and other aspects of the present invention will become evident upon reference to the following detailed description. In addition, as noted above, various references are set forth throughout the present specification that describe in more detail certain procedures or compositions (e.g., plasmids, etc.); all such references are incorporated herein by reference in their entirety.

DETAILED DESCRIPTION OF THE INVENTION

Figure 1:
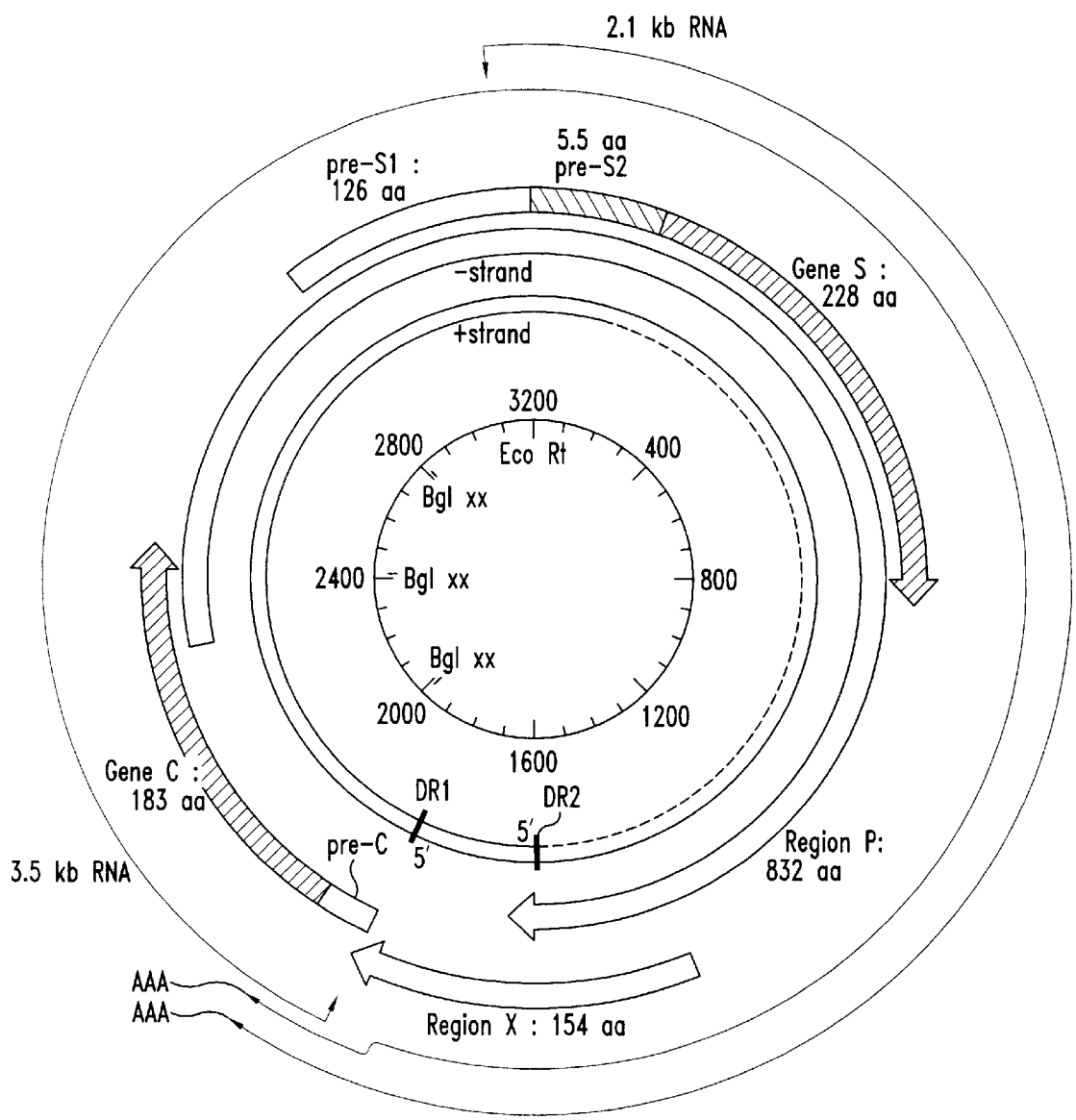
FIG. 1 is a map of the hepatitis B virus (HBV).

The present invention is based on the discovery that the HBcAg of HBV interacts with one or more second proteins, particularly an albumin and/or an unprocessed structural protein from a positive stranded RNA virus, to provide a complex comprised of the HBcAg and the albumin or unprocessed structural protein. Pursuant to such complexing, the HBcAg is believed to undergo conformational changes that enhance the antigenicity of the HBcAg when compared to HBcAg alone, in terms of both or either affinity or specificity. The conformationally changed antigen is recognized by the immune system, which produces antibodies that have a higher specificity and affinity for the HBcAg than are produced using uncomplexed HBcAg.

In accordance with this discovery, the present invention provides improved methods and compositions for the detection and diagnosis of HBV wherein the assays utilize a complexed HBcAg. The present invention also provides antibodies produced using the complexed HBcAg.

The advantages in antigenicity and epitopic configuration in the complexed HBcAg also provide enhanced methods and compositions for the induction of immune responses in an animal. These responses may be humoral, cellular or both. Thus, the present invention provides enhanced vaccination of such an animal. Accordingly, the present invention features compositions and methods utilizing complexed, conformationally changed HBcAgs. The complex provides a synergistic effect when compared to the effect of an HBcAg alone, and will enhance the reaction of the conformationally changed HBcAg with its corresponding antibodies by at least about 1.1, and preferably at least about 1.25, 1.5 or 2.0 times more strongly when compared to the reaction of such antibodies to the HBcAg alone, when the OD value is measured at 492 nm in a spectrophotometer. The present invention also provides antibodies against complexed HBcAg. These and other aspects and features of the present invention are discussed further below.

The term "HBcAg" is used herein in its traditional sense to indicate the core antigen of HBV, which antigen is also known as p22. Principles and Practice of Clinical Virology, 3rd Edition, Chapter 2: Hepatitis Viruses, pp. 167–168. The HBcAg can be either recombinant or purified from a native source. The HBcAg is capable of forming a complex with a serum albumin or a core-like antigen-adjacent protein, which complex, as discussed above, enhances the antigenicity of the HBcAg. Determination of whether the HBcAg has formed such a complex with the serum albumin or core-like antigen-adjacent protein can be determined by mixing the HBcAg with the serum albumin or core-like antigen-adjacent protein in a coating buffer such as TNSCN, TNEU, carbonate buffer, TNSDS or PBS, and then determining whether a dimer, trimer, multimer, or other oligomer has been formed comprising one or more HBcAgs and one or more serum albumins or core-like antigen-adjacent proteins.

A "core-like" protein of a positive stranded RNA virus is a structural protein that provides the same type of functions as the core protein of HCV. Examples of "core-like" proteins from other viruses include the Japanese encephalitis virus core protein and the HIV gag protein. A "core-like antigen" protein is a structural "core-like" protein that includes the portion of the core-like protein that displays the antigenicity of the core-like protein. Regions of the core-like proteins that can be important to antigenicity are well known in the art (see, e.g., Okamoto, et al. *J. Virol.* 188:331, 1992; Wang, U.S. Pat. No. 5,106,726). A core-like antigen protein may be determined for a desired positive-stranded RNA virus, for example, by ELISA or western blotting, or both, for traditional core-type antigenic reactivity, as is well known in the art. A core-like antigen protein may also be determined by SDS-PAGE followed by amino acid sequencing.

Typically, the core-like antigen protein is joined, or fused, to an amino-terminal portion of the adjacent protein or peptide region of the positive-stranded RNA virus to provide an unprocessed "core-like antigen-adjacent protein." Core-like antigen-adjacent proteins are discussed in WO 96/37606 and WO 96/38474. In some embodiments, particularly where the core-like protein is not the first protein region of the polyprotein, the core-like protein is joined to a carboxyl-terminal portion of the adjacent protein of the positive-stranded RNA virus in unprocessed form to provide the inventive unprocessed core-like antigen-adjacent protein of the invention. In unprocessed form means that the core-like region and the adjacent region are typically, and preferably, maintained precisely as they are joined (i.e., encoded) in a native positive-stranded RNA virus. As with the polyprotein discussed below and other proteins herein, the core-like antigen protein may be insignificantly modified without changing the inventive functioning of the core-like antigen protein using methods well known in the art.

The portion of the "adjacent protein" that is adjacent the core-like antigen protein is sized such that the fusion protein has an epitopic configuration specific to an unprocessed core-like antigen-adjacent protein of the positive-stranded RNA virus. Thus, typically, the amino-terminal portion of the adjacent protein region must be of sufficient length to permit the fusion protein to display the transient epitopic configuration specific to the unprocessed core-like region. In a preferred embodiment, the core-like antigen-adjacent protein comprises a positive-stranded RNA virus core-like antigen protein joined to an amino-terminal portion of an adjacent protein of the positive-stranded RNA virus wherein the amino-terminal portion of the positive-stranded RNA virus envelope region is sized such that the core-like antigen-adjacent protein has an epitopic configuration specific to an unprocessed core-like antigen-adjacent protein region of the positive-stranded RNA virus.

Determination of whether a given polypeptide displays the epitopic configuration of a core-like antigen-adjacent protein can be performed as follows. A core-like antigen-adjacent protein in question can be included in a panel of core-like antigen-adjacent proteins comprising an established core-like antigen-adjacent protein, such as EN-80-2 (ATCC 55451; WO 96/37606; WO 96/38474). The panel is placed in a series of wells on a microtiter plate. The panel can also include other core-like antigen-adjacent proteins having different lengths of adjacent protein. In a separate well is placed an established nonstructural, or other, protein capable of synergistic cooperation with the core-like antigen-adjacent protein, such as EN-80-1, an NS3-NS4 protein from HCV. An antiserum is selected for the established core-like antigen-adjacent protein that reacts weakly with the established core-like antigen-adjacent protein and that also is nonreactive with the established nonstructural protein. The basis for selection is that the antiserum will react with the separated proteins as expected, but the antiserum will react much more strongly when both a suitable core-like antigen-adjacent protein and the established nonstructural protein are present in the sample. Many examples of such an antiserum, such as G614 (diluted 8-fold), G614 (diluted 16-fold), G615 (diluted 8-fold), G615 (diluted 16-fold), and 8-5, are set forth in WO96/38474. The antiserum is introduced to the sample proteins under conditions suitable for elicitation and detection of a reaction between the antiserum and the given protein, and detect and measure such response. The established nonstructural protein is then combined with a further sample of each member of the core-like antigen-adjacent protein panel. Next, the antiserum is introduced to the combined proteins under conditions suitable for elicitation and detection of a reaction between the antiserum and the proteins, and such response is detected and measured. Those core-like antigen-adjacent proteins that provide a cooperative effect are suitable for use in the present invention. Preferably, the antiserum will react at least about 1.25 or 1.5 times more strongly with the combined proteins when compared to the additive reaction of the antiserum with each protein, alone. Further preferably, the antiserum will react at least about twice as strongly. Each of the above-recited steps is routine in the art, in light of the present specification.

The core-like antigen-adjacent protein is preferably isolated, which means that the core-like antigen-adjacent protein is separated from the remainder of the polyprotein originally translated from the genome of the positive-stranded RNA virus. The core-like antigen-adjacent protein is also preferably separated from its encoding nucleic acid molecule.

An "isolated, substantially complete, unprocessed polyprotein" from a positive-stranded RNA virus is the polyprotein that is initially translated from the genome of the positive-stranded RNA virus. Such polyprotein has not been subjected to processing, and thus the processing sites between the proteins of the polyprotein are not cleaved. The polyprotein is preferably isolated, which means that the polyprotein has been separated from its encoding genome. The polyprotein is substantially complete when it retains all of the functional elements necessary to provide the immune-active features of the present invention, particularly epitopic configuration(s) that are present only in the polyprotein and not in the processed proteins or subunits that are obtained from the polyprotein. However, with respect to this and other proteins of the present invention, it is within the skill of the art to make conservative amino acid substitutions, or insignificant amino acid additions, modifications or deletions, that may change the amino acid sequence of the protein but do not significantly alter the functioning of the protein (i.e., the unprocessed epitopic configuration is retained). However, such modifications may, when desired, delete the processing signals and/or sites of the protein. These modifications are discussed further below. The completeness of the polyprotein may be determined, for example, by SDS-PAGE followed by amino acid sequencing. The completeness may also be determined by utilizing the polyprotein in question in one or more of the assays discussed below, and detecting effects of epitopic configurations specific to the unprocessed state. The polyprotein can be used to complex with the HBcAg in the same manner as the core-like antigen-adjacent proteins herein, and the discussion of such proteins applies also to the polyprotein.

Complexing the unprocessed proteins above with a second protein such as a nonstructural protein results in a synergistic effect that greatly enhances the sensitivity and specificity provided by the unprocessed core region. Thus, in a preferred embodiment the core-like antigen-adjacent protein of the present invention is used complexed with a second protein. The second protein is preferably, but not necessarily, from a positive-stranded RNA virus, and is further preferably from the same positive-stranded RNA virus as the core-like antigen-adjacent protein (such as an NS5 protein or an unprocessed NS3-NS4 fusion protein from HCV when the core-like antigen-adjacent protein is from HCV).

In positive stranded RNA viruses other than HCV, the nonstructural proteins may be referred to by other names, as is well known in the art. For the purposes of the present specification, all such nonstructural-like proteins shall be referred to herein as "nonstructural proteins." As noted above, the nonstructural coding regions of positive-stranded RNA viruses are well known in the art.

The determination of an appropriate second protein that is suitable for use with the core-like antigen-adjacent protein, which second protein may include portions of nonstructural coding regions comprising more than one nonstructural protein (or less than all of one nonstructural protein), can be performed as follows. A second protein in question can be included in a panel of second proteins comprising an established second protein, such as EN-80-2 (HCV core-env). The panel is placed in a series of wells on a microtiter plate. The panel can also include other second proteins having different lengths. In a separate well is placed an established core-like antigen-adjacent protein capable of synergistic cooperation with the established second protein, such as EN-80-1 (HCV NS3-NS4). An antiserum is selected for the established second protein that reacts weakly with the established core-like antigen-adjacent second protein and that also is nonreactive with the established second protein. The basis for selection is that the antiserum will react with the separated proteins as expected, but the antiserum will react much more strongly when both a suitable second protein and the established core-like antigen-adjacent protein are present in the sample. Many examples of such antisera are set forth in WO 96/37606 and WO 96/38474. The antiserum is introduced to the sample proteins under conditions suitable for elicitation and detection of a reaction between the antiserum and the given protein, and such response is detected and measured. The established core-like antigen-adjacent protein is combined with each member of the second protein panel. Next, the antiserum is introduced to the combined proteins under conditions suitable for elicitation and detection of a reaction between the antiserum and the proteins, and such response is detected and measured. Those second proteins that provide a cooperative effect are suitable for use in the present invention. Each of the above-recited steps is routine in the art, in light of the present specification.

The term "positive-stranded RNA virus" is used herein in its traditional sense, and includes viruses such as Togaviridae, Coronaviridae, Retroviridae, Picornaviridae, Caliciviridae and Flaviviridae. Examples of such positive-stranded RNA viruses are discussed in WO 96/37606 and WO 96/38474. Examples of suitable core-envelope fusion proteins include those described in such PCT applications, such as the EN-80-2 core-env fusion protein of HCV (ATCC 55451), the EN-I-5 antigen gag-env antigen from the Human Immunodeficiency Virus (HIV), the H1 core-env antigen of the Human T-cell Leukemia virus (HTLV), and the HPV 16 E7 antigen from the Human Papilloma Virus (HPV).

The term "serum albumin" is used herein in its traditional sense, to indicate a well known protein found in the blood. Serum albumins are secreted into the blood by liver cells, and bind to and solubilize many small molecules that are only slightly soluble in the blood serum absent such binding by the serum albumin. The folding of the polypeptide chain of serum albumin allows disulfide linkages to form between cysteine residues. The protein contains 3 similar protein domains, and is encoded by a gene having 14 introns and 15 exons. Thus, expression of the gene in eukaryotes and prokaryotes generally includes processing mechanisms or is performed using non-intron containing genes, such as cDNA. Darnell et al., *Molecular Cellular Biology*, Sci. Am. Books, 1986. pp. 413–415; Rothschild et al., *The New England Journal of Medicine* 286(14):748–757, 1972; Sjobring et al., *The Journal of Biological Chemistry* 266(1) :399–405, 1991; Tullis, J., *J.A.M.A.* 237(4):355–360, 1977; Tullis, J., *J.A.M.A.* 237(5):460–463, 1977. In preferred embodiments, the serum albumin is human serum albumin, α-fetoprotein, bovine serum albumin, fetal bovine serum albumin, new born bovine serum albumin or mouse serum albumin. Also preferably, the serum albumin is selected from the same species as the sample source or recipient of the HBcAg-albumin complex. However, particularly for in vitro uses such as most diagnostic and detection assays, the albumin can be from another species. The serum albumin can be recombinant, purified from an animal source, or produced synthetically.

"Complex," or aggregate, is also used herein in its traditional sense, to indicate a dimer or multimer formed between an HBcAg and one or more second proteins selected from serum albumins and core-like antigen-adjacent proteins. (See, e.g., WO 95/33053; WO 96/37606; WO 96/38474.) The complex is believed to be formed by protein-protein interactions between the HBcAg and the second protein, as opposed, for example, to fusion of ends of the proteins to one another (as through genetic engineering) or covalent cross-linking by intermediate agents such as glutaraldehyde. "Complex" also refers to an aggregate formed between a core-like antigen-adjacent protein and a second protein. Complexes of the present invention can include larger multimers, and can have molecular weights in excess of 800 kD. Although not required to make or use the present invention, it is believed that the complex may be presented in a micelle form. Upon formation of the complex, it is believed that the conformation of the HBcAg is altered. Thus, the presentation of the HBcAg in the body, in the presence of the defined second protein, is different from the presentation that is found in vitro in the absence of the defined second protein.

In one embodiment, the present invention provides compositions comprising a complexed HBcAg as described above along with one or more different core-like antigen-adjacent proteins from one or more different positive stranded RNA viruses (such core-like antigen-adjacent proteins are preferably complexed with a second protein that causes a synergistic effect in the core-like antigen-adjacent protein that is similar to the synergistic effect described herein for the HBcAg). In preferred embodiments, the complexes comprise at least two or three different core-like antigen-adjacent proteins from different positive-stranded RNA viruses. Such combining of complexed HBcAgs and one or more complexed core-like antigen-adjacent proteins provides assays able to detect more than one target virus (HBV and one or more selected viruses) and multi-valent vaccines.

In a preferred embodiment related to such multi-complex assays complexes from different viruses are bound to different labels, or other wise detectably distinguished (methods of creating such distinguishing features will be apparent to a person of ordinary skill in the art in light of the present specification). This permits a single assay comprising the plurality of antibody-bound complexes to distinguishably detect not only whether a sample contains one of the HBcAg and the positive stranded RNA viruses, but which one (or more) of the viruses is in the sample.

As with other aspects of the present invention, the positive stranded RNA viruses are preferably selected from the group consisting of Togaviridae, Coronaviridae, Retroviridae, Picornaviridae, Caliciviridae and Flaviviridae, further preferably HCV, HIV and HTLV, and in the case where the there are three different positive-stranded RNA viruses, the three are HCV, HIV and HTLV.

With respect to HBcAgs, serum albumins, core-like antigen-adjacent proteins and other proteins of the present invention, as discussed further below, it is within the skill of the art to make conservative amino acid substitutions, or insignificant amino acid additions, modifications, truncations or deletions, that may change the amino acid sequence of the protein but do not significantly alter the functioning of the protein (i.e., the antigenic configuration is retained).

The present invention also provides antibodies, including monoclonal antibodies, to the complexed HBcAgs, as well as other proteins of the present invention. The antibodies can be used, for example, to provide particularly sensitive and specific detection of an HBcAg in a sample.

Still further, the present invention provides compositions and methods for the elicitation of an enhanced immune response in an animal (either humoral, cellular, or both). Even further, the compositions and methods can vaccinate an animal against the pathogenic state, such as HBV virus associated with the HBcAg.

Preferably, the methods and compositions of the present invention, including those for detection, immune response elicitation and vaccination, are applied to a human being or to samples obtained from a human being. The sample can be obtained from blood, urine, sputum, feces, lymph or other traditional sources.

Production of the Proteins of the Invention

As noted above, the HBcAgs, serum albumins and core-like antigen-adjacent proteins of the present invention can be either recombinant or purified from an animal source. Purification can be effected using methods well known in the art, including affinity chromatography, ion exchange ultrafiltration and gel filtration (The National Medical Series For Independent Study, "Chapter 3: Amino Acid and Protein Structure. IV. PURIFICATION OF PROTEINS," *Biochemistry*, 3d ed., pp. 37–42).

Production of the proteins of the present invention can also be effected using recombinant methods, which are generally well known in the art. Within such methods, numerous vector constructs suitable for use with a nucleic acid molecule encoding a desired protein can be prepared as a matter of convenience. Within the context of the present invention, a vector construct is understood to typically refer to a DNA molecule, or a clone of such a molecule (either single-stranded or double-stranded), that has been modified through human intervention to contain segments of DNA combined and juxtaposed in a manner that as a whole would not otherwise exist in nature. Vector constructs of the present invention comprise a first DNA segment encoding a desired protein operably linked to additional DNA segments required for the expression of the first DNA segment. Within the context of the present invention, additional DNA segments will include a promoter and will generally include transcription terminators, and may further include operators, enhancers, mRNA ribosomal binding sites, appropriate sequences that control transcription and translation initiation and termination, and/or other elements. See WO 94/25597; WO 94/25598; Pouwels et al., *Cloning Vectors: A Laboratory Manual*, Elsevier, New York, 1985. The ability to replicate in the desired host cells, usually conferred by an origin of replication, and a selection gene by which transformants are identified, may additionally be incorporated into the vector construct.

Methods for producing recombinant HBcAg, serum albumin and core-like antigen-adjacent protein in a variety of prokaryotic and eukaryotic host cells are generally known in the art (*Methods in Enzymology* 185, Goeddel (ed.), Academic Press, San Diego, Calif., 1990; see also *Methods in Enzymology*, Guthrie and Fink (eds.), Academic Press, San Diego, Calif., 1991), and are discussed in more detail below.

Turning to expression in bacterial hosts, vectors used for such expression will generally contain a selectable marker, such as a gene for antibiotic resistance, and a promoter that functions in the host cell. The expression units may also include a transcriptional terminator. Appropriate promoters include the following promoter systems: trp (Nichols and Yanofsky, *Meth. Enzymol.* 101:155–164, 1983), lac (Casadaban et al., *J. Bacteriol.* 143:971–980, 1980; Chang et al., *Nature* 275:615, 1978; Goeddel et al., *Nature* 281:544, 1979), phage λ (Queen, *J. Mol. Appl. Genet.* 2:1–10, 1983), β-lactamase (penicillinase); tryptophan (trp) (Goeddel et al., *Nucl. Acids Res.* 8:4057, 1980; and EP-A-36776), tac (Maniatis, *Molecular Cloning: A Laboratory Manual*, Cold Spring Harbor Laboratory, p. 412, 1982). Additionally, the phage λ $P_L$ promoter can advantageously combined with a cI857ts thermolabile repressor sequence.

Examples of plasmids useful for transforming prokaryotic hosts include the pUC plasmids (Messing, *Meth. Enzymol.* 101:20–78, 1983; Vieira and Messing, *Gene* 19:259–268, 1982), pBR322 (Bolivar et al., *Gene* 2:95–113, 1977), pCQV2 (Queen, ibid.), pKK223-3 (Pharmacia Fine Chemicals, Uppsala, Sweden), pGEM1 (Promega Biotec, Madison, Wis., USA), pHUB2 (resident in *E. coli* strain JMB9 (ATCC 37092)), pPLc28 (resident in *E. coli* RR1 (ATCC 53082)), and derivatives thereof. Plasmids may contain viral, bacterial and/or eukaryotic elements.

Various prokaryotic host cells may be utilized within the context of the present invention. Generally, preferred prokaryotic host cells should have a well-characterized genetic system, including known cloning vectors and methods of genetic manipulation. Representative examples of such host cells include gram negative or gram positive organisms, for example, *E. coli, Bacillus subtilis, Salmonella typhimurium,* and various other species within the genera Pseudomonas Enterobacteriaceae, Streptomyces, Staphylococcus, Bacillaceae, Salmonella, Shigella, and Corynebacteria. In one preferred embodiment, the host cell is an *E. coli,* which can contain a DE3 lysogen and T7 RNA polymerase, such as BL21(DE3), JM109(DE3) or BL21 (DE3) pLysS. In a prokaryotic host cell such as *E. coli,* a desired protein may include an N-terminal Methionine residue to facilitate expression of the recombinant polypeptide in the prokaryotic host cell. The N-terminal Met may be cleaved from the expressed recombinant protein if desired.

Desirable prokaryotes (and eukaryotes such as those discussed herein) may be readily obtained from a variety of commercial sources including, for example, the American Type Culture Collection (ATCC) (Rockville, Md.). Alternatively, many of the above-described bacteria may be isolated from sources that are known by those of skill in the art to contain such prokaryotes, based upon techniques that are known in the art. (See Bergy's *Shorter Manual of Determinative Bacteriology,* 8th ed., Holt, John G. (ed.), Williams & Wilkins, 1977.)

Recombinant protein produced in prokaryotic culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. RP-HPLC can be employed for final purification steps. Microbial cells can be disrupted by any convenient method, including freeze-thaw cycling, sonication, mechanical disruption, or use of cell lysing agents.

Turning to production of desired protein in eukaryotic cells, eukaryotic host cells suitable for use in practicing the present invention include mammalian, avian, plant, insect and fungal cells such as yeast.

Yeast vectors will often contain an origin of replication sequence from a 2μ yeast plasmid, an autonomously replicating sequence (ARS), a promoter region, sequences for polyadenylation, sequences for transcription termination, and a selectable marker gene. In addition, sequences encoding appropriate signal peptides that are not naturally associated with the desired protein can be incorporated into expression vectors. For example, a DNA sequence for a signal peptide (secretory leader) may be fused in-frame to the sequence encoding the desired protein so that the desired protein is initially translated as a fusion protein comprising the signal peptide. A signal peptide that is functional in the intended host cells enhances extracellular secretion of the desired protein. The signal peptide may be cleaved from the desired protein upon secretion of the desired protein from the cell.

Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et al., *Gene* 107:285–295, 1991; and van den Berg et al., *Bio/Technology* 8:135–139, 1990. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of an HBcAg and other proteins of the present invention. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929. 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems can also be employed to express desired recombinant proteins. Baculovirus systems for production of heterologous proteins in insect cells are reviewed by Luckow and Summers, *Bio/Technology* 6:47, 1988. Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10:2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566. The vectors may be derived from retroviruses. In place of the native signal sequence, a heterologous signal sequence may be added, such as the signal sequence for IL-7 described in U.S. Pat. No. 4,965,195; the signal sequence for IL-2 receptor described in Cosman et al., *Nature* 312:768, 1984; the IL-4 signal peptide described in EP 367,566; the type I IL-1 receptor signal peptide described in U.S. Pat. No. 4,968,607; and the type II IL-1 receptor signal peptide described in EP 460,846.

Preferred eukaryotic cells include cultured mammalian cell lines (e.g., rodent or human cell lines), insect cell lines (e.g., Sf-9) and fungal cells, including species of yeast (e.g., Saccharornyces spp., particularly *S. cerevisiae*, Schizosaccharomyces spp., Kluyveromyces spp., Pichia, and *K. lactis*) or filamentous fungi (e.g., Aspergillus spp., Neurospora spp.).

Techniques for transforming these host cells, and methods of expressing foreign DNA sequences cloned therein, are well known in the art (see, e.g., Maniatis et al., *Molecular Cloning. A Laboratory Manual,* Cold Spring Harbor Laboratory, 1982; Sambrook et al., supra; "Gene Expression Technology," *Methods in Enzymology* 185, Goeddel (ed.), Academic Press, San Diego, Calif., 1990; "Guide to Yeast Genetics and Molecular Biology," *Methods in Enzymology,* Guthrie and Fink (eds.), Academic Press, San Diego, Calif., 1991; Hitzeman et al., *J. Biol. Chem.* 255:12073–12080, 1980, Alber and Kawasaki, *J. Mol. Appl. Genet.* 1:419–434, 1982; Young et al., in *Genetic Engineering of Microorganisms for Chemicals,* Hollaender et al. (eds.), Plenum, N.Y., 1982, p. 355; Ammerer, *Meth. Enzymol.* 101:192–201, 1983; McKnight et al. U.S. Pat. No. 4,935,349).

Transformed yeast host cells are often preferable to mammalian or other eukaryotic systems to express desired protein as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Turning to the sequences of the proteins of the present invention, including HBcAgs, serum albumins and core-like antigen-adjacent proteins, and their encoding nucleic acid molecules, mutations in nucleotide sequences constructed for expression of the proteins preferably preserve the reading frame of the encoding sequences. Furthermore, the mutations preferably do not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution or deletion.

Alternatively, oligonucleotide-directed, site-specific mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and Sambrook et al. (supra).

The primary amino acid structure of the above-described proteins can also be modified by forming conjugates with other chemical moieties, such as glycosyl groups, lipids, phosphate, acetyl groups, or with other proteins or polypeptides, provided that such modifications do not disrupt the antigenicity and/or cooperative properties of the proteins. (See U.S. Pat. No. 4,851,341; see also Hopp et al., *Bio/Technology* 6:1204, 1988.) For example, such modifications should not interfere with the epitopic configuration (including access to the epitope and other antigenic considerations) that is specific to the HBcAg when it is complexed with the serum albumin or core-like antigen-adjacent protein.

Cell-free translation systems can also be employed to produce desired proteins using RNAs derived from DNA constructs disclosed herein.

Antibodies Against The Proteins Of The Invention

The present invention also provides antibodies, i.e., binding partners, such as monoclonal and polyclonal antibodies, directed against the HBcAgs complexed with the serum albumins or core-like antigen-adjacent proteins of the present invention to provide one or both of the immunizing agent or the selective agent. As discussed above, such complexing is believed to induce conformational changes within the HBcAg, thereby providing enhanced specificity and affinity in the antibody produced when compared to that obtained using the HBcAg when not complexed with a serum albumin or core-like antigen-adjacent protein.

Antibodies can be produced by using a protein/aggregate of the invention as an immunogen through standard procedures for preparing a hybridoma, and/or other methods. The resulting antibodies are particularly useful for detecting the HBcAg in a sample, preferably a sample from a human being. See WO 94/25597 and WO 94/25598.

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired protein complex is utilized to immunize the animal, typically through intraperitoneal, intramuscular, intraocular, or subcutaneous injections. The immunogenicity of the protein complex of interest may be increased through the use of an adjuvant such as Freund's complete or incomplete adjuvant. Following several booster immunizations, small samples of serum are collected and tested for reactivity to the desired protein or peptide.

Once the titer of the animal has reached a plateau in terms of its reactivity to the protein, larger quantities of polyclonal antisera may be readily obtained either by weekly bleedings, or by exsanguinating the animal.

Monoclonal antibodies can also be readily generated using well-known techniques (see U.S. Pat. Nos. RE 32,011, 4,902,614, 4,543,439, and 4.411,993, see also *Monoclonal Antibodies, Hybridomas: A New Dimension in Biological Analyses*, Kennett et al. (eds.), Plenum Press, 1980, and *Antibodies: A Laboratory Manual*, Harlow and Lane (eds.), Cold Spring Harbor Laboratory Press, 1988). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another protein such as ovalbumin or keyhole limpet hemocyanin (KLH), or through the use of adjuvants such as Freund's complete or incomplete adjuvants. The initial elicitation of an immune response may be through intraperitoneal, intramuscular, intraocular, or subcutaneous routes.

Between one and three weeks after the initial immunization, the animal may be reimmunized with booster immunization. The animal may then be test bled and the serum tested for binding to the unprocessed polypeptide using assays as described above. Additional immunizations may also be accomplished until the animal has reached a plateau in its reactivity to the desired protein or peptide. The animal may then be given a final boost of the desired protein or peptide, and three to four days later sacrificed. At this time, the spleen and lymph nodes may be harvested and disrupted into a single cell suspension by passing the organs through a mesh screen or by rupturing the spleen or lymph node membranes which encapsulate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the protein or peptide of interest that is suitable for generating an immune response as described above. Subsequently, the lymphocytes are harvested and fused as described below.

Cells that are obtained through the use of in vitro immunization or from an immunized animal as described above may be immortalized by transfection with a virus such as the Epstein-Barr Virus (EBV). (>See Glasky and Reading, *Hybridoma* 8(4):377–389, 1989.) Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas,* 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag0.2.3 (ATCC No. CRL 1631), and YB2/0 (ATCC No. CRL 1662). Preferred fusion lines include NS-1 (ATCC No. TIB 18) and P3X63-Ag 8.653 (ATCC No. CRL 1580), which may be utilized for fusions with either mouse, rat, or human cell lines. Fusion between the myeloma cell line and the cells from the immunized animal can be accomplished by a variety of methods, including the use of polyethylene glycol (PEG) (see *Antibodies: A Laboratory Manual,* supra) or electrofusion (see Zimmerman and Vienken, *J. Membrane Biol.* 67:165–182, 1982).

Following the fusion, the cells are placed into culture plates containing a suitable medium, such as RPMI 1640 or DMEM (Dulbecco's Modified Eagles Medium, JRH Biosciences, Lenexa, Kan.). The medium may also contain additional ingredients, such as fetal bovine serum (FBS, e.g., from Hyclone, Logan, Utah, or JRH Biosciences), thymocytes that were harvested from a baby animal of the same species as was used for immunization, or agar to solidify the medium. Additionally, the medium should contain a reagent which selectively allows for the growth of fused spleen and myeloma cells. Particularly preferred is the use of HAT medium (hypoxanthine, aminopterin, and thymidine) (Sigma Chemical Co., St. Louis, Mo.). After about seven days, the resulting fused cells or hybridomas may be screened in order to determine the presence of antibodies which recognizes the proteins of the present invention. Following several clonal dilutions and reassays, a hybridoma producing antibodies that bind to the protein of interest can be isolated.

Other techniques can also be utilized to construct monoclonal antibodies. (See Huse et al., "Generation of a 1Large Combinational Library of the Immunoglobulin Repertoire in Phage Lambda," *Science* 246:1275–1281, 1989; Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, 1989; Alting-Mees et al., "Monoclonal Antibody Expression Libraries: A Rapid Alternative to Hybridomas." *Strategies in Molecular Biology* 3:1–9, 1990; these references describe a commercial system available from Stratacyte, La Jolla, Calif., which enables the production of antibodies through recombinant techniques.) Briefly, mRNA is isolated from a B cell population and utilized to create heavy and light chain immunoglobulin cDNA expression libraries in the λIMMUNOZAP(II) and λIMMUNOZAP(L) vectors. These vectors may be screened individually or co-expressed to form Fab fragments or antibodies (see Huse et al., supra; Sastry et al., supra). Positive plaques can subsequently be converted to a non-lytic plasmid that allows high level expression of monoclonal antibody fragments from *E. coli.*

Similarly, antibodies can also be constructed utilizing recombinant DNA techniques to incorporate the variable regions of a gene that encode a specifically binding antibody. The construction of these antibodies can be readily accomplished by one of ordinary skill in the art given the disclosure provided herein. (See Larrick et al., "Polymerase Chain Reaction Using Mixed Primers: Cloning of Human Monoclonal Antibody Variable Region Genes From Single Hybridoma Cells," *Biotechnology* 7:934–938, 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989; see also U.S. Pat. No. 5,132,405 entitled "Biosynthetic Antibody Binding Sites.") Briefly, in one embodiment, DNA segments encoding the desired protein or peptide interest-specific antigen binding domains are amplified from hybridomas that produce a specifically binding monoclonal antibody, and are inserted directly into the genome of a cell that produces human antibodies. (Slee Verhoeyen et al., supra; see also Reichmann et al., supra.) This technique allows the antigen-binding site of a specifically binding mouse or rat monoclonal antibody to be transferred into a human antibody. Such antibodies are preferable for therapeutic use in humans because they are not as antigenic as rat or mouse antibodies.

Monoclonal antibodies and other antibodies can be produced in a number of host systems, including tissue cultures, bacteria, eukaryotic cells, plants and other host systems known in the art.

Once suitable antibodies have been obtained, they may be isolated or purified by many techniques well known to those of ordinary skill in the art (see *Antibodies: A Laboratory Manual,* Harlow and Lane (eds.), Cold Spring Harbor Laboratory Press, 1988; U.S. Pat. No. 4,736,110; and U.S. Pat. No. 4,486,530). Suitable isolation techniques include peptide or protein affinity columns, HPLC or RPHPLC, purification on protein A or protein G columns, or any combination of these techniques. Within the context of the present invention, the term "isolated" as used to define antibodies means substantially free of other blood components.

The antibodies of the present invention have many uses. As discussed further below, the antibodies of the present invention are particularly useful for the detection and diagnosis of HBcAgs, and therefore HBV, as well as the detection of core-like antigen-adjacent proteins and the positive stranded RNA viruses associated therewith. Other uses include, for example, flow cytometry to sort cells displaying one more of these antigens. Briefly, in order to detect the desired antigen(s) of interest on cells, the cells are incubated with a labeled monoclonal antibody which specifically binds to the protein of interest, followed by detection of the presence of bound antibody. These steps may also be accomplished with additional steps such as washings to remove unbound antibody. Labels suitable for use within the present invention are well known in the art including, among others, flourescein isothiocyanate (FITC), phycoerythrin (PE), horse radish peroxidase (HRP), and colloidal gold. Particularly preferred for use in flow cytometry is FITC, which may be conjugated to a purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; Goding, "Conjugation of Antibodies with Fluorochromes: Modification to the Standard Methods," *J. Immunol. Methods* 13:215–226, 1970.)

Assays For The Detection Of An HBcAg, Or Antibodies Against HBcAg, In A Sample

As noted above, the present invention provides methods, or assays, for detecting an HBcAg and/or one or more core-like antigen-adjacent proteins from RNA viruses in a sample. The present invention also provides methods of detecting antibodies produced against an HBcAg and/or such one or more core-like antigen-adjacent proteins. The methods are characterized by the ability of the complexed HBcAg of the present invention to be bound by antibodies against the HBcAg, and the ability of antibodies produced against the complexed HBcAg of the present invention to bind to HBcAgs in a sample. In addition, it has been found that, if desired, one or more core-like antigen-adjacent proteins can be specifically detected in the same assay as the HBcAg; the effect is particularly preferred where the core-like antigen-adjacent protein is complexed with a second protein other than an HBcAg, preferably a nonstructural protein of a positive stranded RNA virus (further preferably the same species of positive stranded RNA virus from which the core-like antigen-adjacent protein is obtained). Such complexing of core-like antigen-adjacent protein with a second protein is set forth in WO 96/37606 and WO 96/38474, and provides synergistically enhanced antigenicity for the core-like antigen-adjacent protein.

Surprisingly, the complexed HBcAg, or antibodies produced against the complex, of the present invention provides significantly enhanced detection of HBcAg. In particular, the use of a complexed HBcAg in the assay provides a synergistic effect that permits significantly more sensitive detection of the HBcAg than when either the HBcAg is utilized alone. Also surprisingly, when the complex is used in assays with one or more, and preferably two or three, core-like antigen-adjacent proteins (which are preferably also complexed to a second protein, typically other than the HBcAg), the assays also provide methods for selectively, specifically detecting the different proteins, or antibodies against the proteins. In another preferred embodiment, the assay comprises two or more of the core-like antigen-adjacent proteins (preferably also complexed), but does not comprise the HBcAg, and the assay is capable of specifically detecting each of the two or more core-like antigen-adjacent proteins (and therefore the corresponding positive stranded RNA viruses). The following discussion concerning assays for HBcAg, as well other discussion herein relating to HBcAg such as for immuno-induction purposes, also applies to the core-like antigen-adjacent proteins.

In a preferred embodiment, the multi-complex assays comprise different labels, discussed generally below, for each of the different complexes so that a single assay can distinguish between a selected variety of target antigens.

A preferred assay for the detection of the target antigen is a sandwich assay such as an enzyme-linked immunosorbent assay (ELISA). In one preferred embodiment, the ELISA comprises the following steps: (1) coating target antigen complexed with at least one serum albumin or core-like antigen-adjacent protein onto a solid phase, (2) incubating or contacting a sample suspected of containing antibodies against the complexed HBcAg coated onto the solid phase under conditions and for a time sufficient to allow the formation of an antigen-antibody complex, or antibody-bound complex, (3) adding an anti-antibody (such as anti-IgG) conjugated with a label to be captured by the resulting antigen-antibody complex bound to the solid phase, and (4) detecting the captured label and determining therefrom whether the sample has antibodies against the HBcAg.

Although a preferred assay is set forth above, a variety of assays can be utilized in order to detect antibodies that specifically bind to an HBcAg in a sample, or to detect an HBcAg bound to one or more antibodies from the sample. Exemplary assays are described in detail in *Antibodies. A Laboratory Manual,* Harlow and Lane (eds.), Cold Spring Harbor Laboratory Press, 1988. Representative examples of such assays include: countercurrent immuno-electrophoresis (CIEP), radioimmunoassays, radioimmunoprecipitations, enzyme-linked immunosorbent assays (ELISA), dot blot assays, inhibition or competition assays, sandwich assays, immunostick (dip-stick) assays, simultaneous assays, immunochromatographic assays, immunofiltration assays, latex bead agglutination assays, immunofluorescent assays, biosensor assays, and low-light detection assays (see U.S. Pat. Nos. 4,376,110 and 4,486,530; WO 94/25597; WO/25598; see also *Antibodies. A Laboratory Manual,* supra).

A fluorescent antibody test (FA-test) uses a fluorescently labeled antibody able to bind to one of the HBcAgs of the invention. For detection, visual determinations are made by a technician using fluorescence microscopy, yielding a qualitative result. In one embodiment, this assay is used for the examination of tissue samples or histological sections.

In latex bead agglutination assays, antibodies made using the HBcAg-serum albumin complex of the present invention are conjugated to latex beads. The antibodies conjugated to the latex beads are then contacted with a sample under conditions permitting the antibodies to bind to HBcAgs in the sample, if any. The results are then read visually, yielding a qualitative result. In one embodiment, this format can be used in the field for on-site testing.

Enzyme immunoassays (EIA) include a number of different assays able to utilize the antibodies provided by the present invention. For example, a heterogeneous indirect EIA uses a solid phase coupled with an antibody of the invention and an affinity purified, anti-IgG immunoglobulin preparation. Preferably, the solid phase is a polystyrene microtiter plate. The antibodies and immunoglobulin preparation are then contacted with the sample under conditions permitting antibody binding, which conditions are well known in the art. The results of such an assay can be read visually, but are preferably read using a spectrophotometer, such as an ELISA plate reader, to yield a quantitative result. An alternative solid phase EIA format includes plastic-coated ferrous metal beads able to be moved during the procedures of the assay by means of a magnet. Yet another alternative is a low-light detection immunoassay format. In this highly sensitive format, the light emission produced by appropriately labeled bound antibodies are quantitated automatically. Preferably, the reaction is performed using microtiter plates.

In an alternative embodiment, a radioactive tracer is substituted for the enzyme mediated detection in an EIA to produce a radioimmunoassay (RIA).

In a capture-antibody sandwich enzyme assay, the HBcAg is bound between an antibody attached to a solid phase, preferably a polystyrene microtiter plate, and a labeled antibody. Preferably, the results are measured using a spectrophotometer, such as an ELISA plate reader. This assay is one preferred embodiment for the present invention.

In a sequential assay format, reagents are allowed to incubate with the capture antibody in a step-wise fashion. The test sample is first incubated with the capture antibody. Following a wash step, an incubation with the labeled antibody occurs. In a simultaneous assay, the two incubation periods described in the sequential assay are combined. This eliminates one incubation period plus a wash step.

A dipstick/immunostick format is essentially an immunoassay except that the solid phase, instead of being a polystyrene microtiter plate, is a polystyrene paddle or dipstick. Reagents are the same and the format can either be simultaneous or sequential.

In a chromatographic strip test format, a capture antibody and a labeled antibody are dried onto a chromatographic strip, which is typically nitrocellulose or nylon of high porosity bonded to cellulose acetate. The capture antibody is usually spray dried as a line at one end of the strip. At this end there is an absorbent material that is in contact with the strip. At the other end of the strip the labeled antibody is deposited in a manner that prevents it from being absorbed into the membrane. Usually the label attached to the antibody is a latex bead or colloidal gold. The assay may be initiated by applying the sample immediately in front of the labeled antibody.

Immunofiltration/immunoconcentration formats combine a large solid phase surface with directional flow of sample/reagents, which concentrates and accelerates the binding of antigen to antibody. In a preferred format, the test sample is preincubated with a labeled antibody then applied to a solid phase such as fiber filters or nitrocellulose membranes or the like. The solid phase can also be precoated with latex or glass beads coated with capture antibody. Detection of analyte is the same as standard immunoassay. The flow of sample/reagents can be modulated by either vacuum or the wicking action of an underlying absorbent material.

A threshold biosensor assay is a sensitive, instrumented assay amenable to screening large numbers of samples at low cost. In one embodiment, such an assay comprises the use of light addressable potentiometric sensors wherein the reaction involves the detection of a pH change due to binding of the desired protein by capture antibodies, bridging antibodies and urease-conjugated antibodies. Upon binding, a pH change is effected that is measurable by translation into electrical potential ($\mu$volts). The assay typically occurs in a very small reaction volume, and is very sensitive. Moreover, the reported detection limit of the assay is 1,000 molecules of urease per minute.

Compositions And Methods For The Elicitation Of An Immune Response Against A Complexed HBcAg The present invention also provides compositions and methods for the elicitation of an immune response to the complexed HBcAg, which response may be either humoral, cellular, or both. Preferably, the immune response is induced by a vaccine, and is therefore an immunoprotective immune response. These compositions and methods typically involve an immunogen comprising a complexed HBcAg of the present invention in combination with a pharmaceutically acceptable carrier or diluent. The compositions can also include a cocktail of a complexed HBcAg and one or more, and preferably two or three, core-like antigen-adjacent proteins (which are preferably also complexed to a second protein, typically other than the HBcAg) so that multiple disease states can be affected, or so that multiple aspects of a single disease state can be affected.

In another preferred embodiment, the immunoactive compositions comprise two or more of the core-like antigen-adjacent proteins (which are preferably also complexed to a second protein other than the HBcAg), but do not comprise the HBcAg, and the composition is capable of specifically inducing an immune response to each of the two or more core-like antigen-adjacent proteins (and therefore the corresponding positive stranded RNA viruses). The following discussion concerning immunoactive compositions for HBcAg also applies to the core-like antigen-adjacent proteins.

The HBcAg may comprise an inactivated preparation or an attenuated preparation.

Accordingly, another aspect of the present invention provides a complexed HBcAg capable of eliciting an immune response, preferably capable of immunizing an animal. As will be understood by one of ordinary skill in the art, with respect to the complexed HBcAgs of the present invention, slight deviations of the amino acid sequences can be made without affecting the immunogenicity of the immunogen. Substantial equivalents of the complexed HBcAgs include conservative substitutions of amino acids that maintain substantially the same charge and hydrophobicity as the original amino acid. Conservative substitutions include replacement of valine for isoleucine or leucine, and aspartic acid for glutamic acid, as well as other substitutions of a similar nature (see Dayhoff et al. (eds.), "Atlas of Protein Sequence and Structure," *Natl. Biomed. Res. Fdn.,* 1978).

As will be evident to one of ordinary skill in the art, the immunogens listed above, including their substantial equivalents, may stimulate different levels of response in different animals. The immunogens listed above, including their substantial equivalents, can be tested for effectiveness as a vaccine. These tests include T-cell proliferation assays, determination of lymphokine production after stimulation, and immunoprotection trials. Briefly, T-cell proliferation assays can be utilized as an indicator of potential for cell-mediated immunity. Additionally, evidence of lymphokine production after stimulation by an immunogen can be utilized to determine the potential for protection provided by an immunogen.

Finally, as described below, actual immunoprotection trials can be performed in order to determine protection in animals. In the case of humans, however, instead of immunoprotection trials it is preferred to first screen peripheral blood lymphocytes (PBLs) from patients infected with HBV (or other pathogenic agents where core-like antigen-adjacent proteins are targeted) in the following manner. Briefly, PBLs can be isolated from diluted whole blood using Ficoll density gradient centrifugation and utilized in cell proliferation studies with [$^3$H]-thymidine as described below. Positive peptides are then selected and utilized in primate trials.

The immunogens, or polypeptides, of the present invention can be readily produced utilizing many other techniques well known in the art (see Sambrook et al., supra, *Molecular Cloning, A Laboratory Manual,* Cold Spring Harbor Laboratory Press, 1989).

For purposes of the present invention, warm-blooded animals include, among others, humans, primates, rabbits and mice, chickens and other fowl, cats and dogs, cattle and horses.

Immunogens comprising the complexed HBcAg of the present invention in combination with a pharmaceutically acceptable carrier or diluent can be administered to a patient in accordance with a number procedures known in the art. See WO 94/25597 and WO 94/25598.

Many suitable carriers or diluents can be utilized in the present invention, including among others saline, buffered saline, and saline mixed with nonspecific serum albumin. The pharmaceutical composition may also contain other excipient ingredients, including adjuvants, buffers, antioxidants, carbohydrates such as glucose, sucrose, or dextrins, and chelating agents such as EDTA. The serum albumin itself acts as an adjuvant, thereby enhancing the immune response to the HBcAg, and other adjuvants may also be utilized along with the immunogen, if desired. Examples of such adjuvants include alum or aluminum hydroxide for humans.

The amount and frequency of administration can be determined in clinical trials, and may depend upon such factors as the nature of the complexed HBcAg, the degree of protection required, and other considerations. In one embodiment, immunizations can involve oral administration. Alternatively, the vaccine can be parenterally administrated via the subcutaneous route, or via other routes. Depending upon the application, quantities of injected immunogen will vary from 50 μg to several milligrams in combination with a pharmaceutically acceptable carrier or diluent, and will typically vary from about 100 μg to 1 mg. Booster immunizations can be given from 4–6 weeks later. Preferably, the complexed HBcAg is administered to the upper arm or the anterolateral aspect of the thigh, and not the buttock. Principles and Practice of Clinical Virology, 3rd Edition, Chapter 2: Hepatitis Viruses, p. 175.

Kits For Implementation Of The Various Aspects Of The claimed Invention

The present invention further provides kits for analyzing samples for the presence of HBcAgs or antibodies. The kits comprise a complexed HBcAg, or antibody against the same, and an appropriate solid phase. Preferably, the complexed HBcAg, or corresponding antibody, is bound to the solid phase. The kits can also provide one or more reagents and/or devices for the detection of the complexed HBcAg, or the antibodies. A variety of formats, reagents and devices for inclusion within the kits, including labels or other mechanisms for detecting the antigens or antibodies, are discussed herein.

The present invention also provides kits for the induction of an immune response. The kits comprise compositions comprising a complexed HBcAg of the invention in combination with an pharmaceutically acceptable carrier or diluent, and can also provide devices for administering or assisting in the administration of the composition.

The kits can also include one or more core-like antigen-adjacent proteins from one or more respective positive stranded RNA viruses (which core-like antigen-adjacent proteins are preferably complexed with a second protein that causes a synergistic effect in the core-like antigen-adjacent protein that is similar to the synergistic effect described herein for the HBcAg). Additionally, the kits can also comprise two more of the core-like antigen-adjacent proteins from two or more different positive stranded RNA viruses but without any HBcAg (the core-like antigen-adjacent proteins are preferably complexed as described elsewhere herein).

Other kits suitable for use with the features of the present invention are also provided herewith.

The following Examples are offered by way of illustration, and not by way of limitation.

EXAMPLES

Example 1

Elisa For The Detection Of Antibodies Specific for HBcAg Complexed To A Core-Like Antigen Adjacent Protein An ELISA was used to test samples from HBV, HCV and HTLV-1 positive and negative patients for the presence of antibodies against HBcAg, and core-like antigen-adjacent proteins from HCV and HTLV-1. The ELISA was performed as follows.

(A) Treatment of Microtiter Plate

A microtiter plate was coated with an HBcAg ("A5") complexed with one or more core-like antigen-adjacent proteins and/or a nonstructural protein from two different positive stranded RNA viruses, HCV and HTLV-1, which are discussed further below. In certain of the assays, the core-like antigen-adjacent proteins ("EN-80-2" from HCV and "H1" from HTLV-1) were also complexed with the nonstructural protein from ("EN-80-1" from HCV). The complexes of the invention were coated at appropriate concentrations and blocked with a buffer containing bovine serum albumin. The treated microtiter plate was stored at 2–8° C.

(B) Preparation of Anti-hIgG:HRPO Conjugate

Purified anti-human Immunoglobulin G (anti-hIgG) was conjugated with horse radish peroxidase (HRPO) using $NaIO_4$ to obtain the anti-IgG:HRPO conjugate. The conjugate was purified by chromatography.

(C) Components of Reagents (a) Wash Solution: Phosphate Buffer containing 0.9% NaCl and Thimerosal.

(b) Anti-hIgG:HRPO Conjugate Solution: the anti-hIgG:HRPO conjugate prepared as described above dissolved in Tris Buffer containing a proteineous stabilizer and antiseptics.

(c) Sample Diluent: Tris Buffer containing a proteineous stabilizer and antiseptics.

(d) OPD Substrate Solution: o-phenylene diamine (OPD) dissolved in citrate-phosphate buffer containing $H_2O_2$. (If the solution becomes orange, it means that the solution has been contaminated and cannot be used any more.)

(e) Stopping Solution: 2N $H_2SO_4$ solution.

(f) Positive/Negative controls: the serum samples of persons infected with/without hepatitis C diluted with phosphate buffer containing a proteineous stabilizer and antiseptics at an appropriate concentration.

(D) Procedure:

(a) One hundred and fifty microliters (μl) of the test samples were diluted with Sample Diluent (1:10), and Positive/Negative Controls were added into the wells of the treated microtiter plate. Some wells were retained as substrate blanks.

(b) The plate was gently mixed by shaking and incubated at 37–40° C. for 1 hour.

(c) The plate was washed three times with 0.3 ml of Wash solution per well.

(d) One hundred pi of anti-hIgG:HRPO Conjugate Solution was added to each well.

(e) The plate was gently mixed by shaking and incubated at 37–40° C. for 30 minutes.

(f) The plate was washed five times.

(g) One hundred μl of OPD Substrate Solution was added to each well and the plate was incubated at 15–30° C. in the dark for 30 minutes.

(h) One hundred μl of Stopping Solution was added to each well and gently mixed to stop the reaction.

(i) The OD value per well was measured at 492 nm in a spectrophotometer.

body negative serum; POOL and SP, which were anti-HTLV-1 antibody positive, anti-HCV antibody negative sera; S5, S4, S3 and S2, which were anti-HBcAg antibody positive samples diluted in new born bovine serum (NBBS), and that were anti-HCV and anti-HTLV-1 antibody negative sera; and NC, which was an anti-HCV, anti-HTLV-1 and anti-HBc antibody negative serum.

TABLE 1

| I.D. | 01 | 02 | H1 | A5 | 01 + 02 | 01 + H1 | 01 + A5 | A5 + 02 | A5 + H1 | 01 + 02 + A5 | 01 + 02 + H1 + A5 |
|---|---|---|---|---|---|---|---|---|---|---|---|
| POOL 50X@ | 0.010# | 0.008 | 0.444 | 0.011 | 0.006 | 0.758 | 0.028 | 0.026 | 0.444 | 0.032 | 0.827 |
| SP 40X | 0.008 | 0.004 | 0.374 | 0.000 | 0.002 | 0.708 | 0.014 | 0.013 | 0.405 | 0.032 | 0.834 |
| 80X | 0.012 | 0.010 | 0.158 | 0.025 | 0.007 | 0.239 | 0.041 | 0.054 | 0.217 | 0.075 | 0.300 |
| NC | 0.011 | 0.015 | 0.015 | 0.011 | 0.006 | 0.024 | 0.020 | 0.011 | 0.022 | 0.009 | 0.028 |
| 7-23 40X@ | 0.022 | 1.458 | 0.009 | 0.003 | 1.700 | 0.019 | 0.021 | 1.214 | 0.009 | >2.0 | 1.646 |
| 80X | 0.013 | 0.543 | 0.010 | 0.011 | 0.716 | 0.012 | 0.019 | 0.518 | 0.008 | 0.869 | 0.729 |
| 160X | 0.009 | 0.179 | 0.010 | 0.011 | 0.226 | 0.010 | 0.013 | 0.159 | 0.007 | 0.281 | 0.212 |
| 320X | 0.004 | 0.062 | 0.005 | 0.004 | 0.073 | 0.006 | 0.007 | 0.060 | 0.007 | 0.091 | 0.068 |
| 640X | 0.006 | 0.024 | 0.004 | 0.007 | 0.032 | 0.005 | 0.007 | 0.023 | 0.005 | 0.038 | 0.027 |
| S5 | 0.006 | 0.007 | 0.007 | 0.952 | 0.008 | 0.003 | >2.0 | >2.0 | >2.0 | 1.935 | 1.756 |
| S4 | 0.006 | 0.008 | 0.010 | 0.683 | 0.004 | 0.012 | 1.640 | 1.582 | 1.533 | 1.471 | 1.308 |
| S3 | 0.008 | 0.007 | 0.008 | 0.468 | 0.004 | 0.005 | 0.870 | 0.871 | 0.801 | 0.864 | 0.836 |
| S2 | 0.008 | 0.010 | 0.008 | 0.239 | 0.009 | 0.008 | 0.413 | 0.370 | 0.418 | 0.430 | 0.412 |
| NBBS | 0.008 | 0.009 | 0.009 | 0.010 | 0.007 | 0.009 | 0.015 | 0.009 | 0.006 | 0.006 | 0.011 |

@: positive samples diluted with sample diluent.
: Absorbance at 492 nm.

(E) Determination:

The $OD_{492nm}$ value per well subtracts the mean of the readings of the blanks (backgrounds). The difference (PCx-NCx) between the mean of the readings of the positive controls (PCx) and that of the negative controls (NCx) is equal to or more than 0.5.

The Cut-off value (CO) is calculated by the following formula:

$$CO=PCx \times 0.15+NCx$$

When the readings from test samples were less than the CO value, the samples were considered negative (i.e., HBV, HCV and HTLV-1 antibodies could not be detected in the samples).

When the readings of test samples were equal to or more than the CO value, the samples were considered to be positive; however, it is preferred to repeat the assay for the samples in duplicate. If the readings of either of the duplicate samples were less than the CO value, the samples were considered to be negative. If the duplicate samples were both more than or equal to the Cut-off value, the samples were considered to be positive.

When the readings of test samples were more than NCx but less than the CO value by 20%, the samples were regarded as questionable samples and the assay should be repeated for those samples.

Table 1 shows such enzyme immunoassay to detect the presence of anti-HCV and/or anti-HTLV-1 and/or anti-HBcAg antibodies in human serum. The antigens used for the assay were an HCV NS5 protein (the EN-80-1 antigen; "01" in Table 1 below), an HCV core antigen-envelope protein (the EN-80-2 antigen; "02" in Table 1 below), an HTLV-1 core-env protein (the EN-H-1 antigen; "H1" in Table 1 below) and an HBV core antigen (HBcAg, the A5 antigen; "A5" in Table 1 below).

The samples for the assay were 7–23, which was anti-HCV antibody positive, anti-HTLV-1 and anti-HBcAg anti-

EXAMPLE 2

ELISA for the Detection of Antibodies Specific for HBcAg Complexed to Human Serum Albumin An assay was performed as set forth in the Example 1, above, except that the A5 HBcAg from the Hepatitis B Virus (HBV) was mixed with the HSA in TNEU buffer to provide a complex of the HSA and the HBcAg of HBV. The samples for the assay were as follows. Anti-HBc positive samples were SP and N639. Anti-HBc negative samples were NC1 and NC2.

TABLE 2

| Solid Phase | HSA | A5 | HSA & A5 |
|---|---|---|---|
| SP 2X @ | 0.024# | 1.096 | >2.0 |
| 4X | 0.011 | 0.897 | 1.086 |
| 8X | 0.007 | 0.389 | 0.578 |
| 16X | 0.011 | 0.333 | 0.548 |
| 32X | 0.000 | 0.193 | 0.204 |
| 0X | 0.017 | 0.005 | 0.010 |
| NC 1 | 0.012 | 0.009 | 0.015 |
| NC 2 | 0.026 | 0.018 | 0.031 |
| N639 | 0.014 | 0.881 | 1.715 |
| N639 2X | 0.024 | 0.803 | 1.280 |

@: Anti-HBc positive samples diluted with recalcified human serum, non-reactive for HBV, HCV and HIV.
: Absorbance at 492 nm.

From the foregoing, it will be appreciated that, although specific embodiments of the invention have been described herein for purposes of illustration., various modifications may be made without deviating from the spirit and scope of the invention. Accordingly, the invention is not limited except as by the appended claims.

What is claimed is:

1. An assay for the detection of an antibody against an HBcAg or an independent core-like antigen-adjacent protein of a positive stranded RNA virus in a sample, comprising:

(a) providing an HBcAg complexed with a protein selected from the group consisting of a serum albumin and a core-like antigen-adjacent protein of a positive stranded RNA virus, to provide an HBcAg-protein complex, and providing an independent core-like antigen-adjacent protein of a positive stranded RNA virus complexed to a protein, to provide an independent core-like antigen-adjacent protein complex;

(b) contacting the HBcAg-protein complex and the independent core-like antigen-adjacent protein complex with the sample under conditions suitable and for a time sufficient for the HBcAg-protein complex and the independent core-like antigen-adjacent protein complex to bind to one or more antibodies against the HBcAg or the independent core-like antigen-adjacent protein present in the sample, thereby providing one or more antibody-bound complexes; and (c) detecting the one or more antibody-bound complexes, and therefrom determining whether the sample contains an antibody against HBcAg or the independent core-like antigen-adjacent protein.

2. The assay of claim 1 wherein the step of detecting allows the differentiation between different antibody-bound complexes.

3. The assay of claim 1 or 2 wherein the step of providing comprises providing at least two independent core-like antigen-adjacent proteins, at least two of which are from different positive-stranded RNA viruses, and wherein the step of contacting is performed under conditions suitable and for a time sufficient for each of the HBcAg and the at least two independent core-like antigen-adjacent proteins to bind to one or more antibodies specific therefor, thereby providing one or more antibody-bound complexes.

4. The assay of claim 1 or 2 wherein the step of providing comprises providing at least three independent core-like antigen-adjacent proteins, at least three of which are from different positive-stranded RNA viruses, and wherein the step of contacting is performed under conditions suitable and for a time sufficient for each of the HBcAg and the at least three independent core-like antigen-adjacent proteins to bind to one or more antibodies specific therefor, thereby providing one or more antibody-bound complexes.

5. The assay of claim 1 or 2 wherein the positive stranded RNA virus is selected from the group consisting of Togaviridae, Coronaviridae, Retroviridae, Picornaviridae, Caliciviridae and Flaviviridae.

6. The assay of claim 1 or 2 wherein the positive-stranded RNA virus is selected from the group consisting of hepatitis C virus (HCV), Human Immunodeficiency virus (HIV) and Human T-cell Leukemia virus (HTLV).

7. The assay of claim 3 wherein the two different positive-stranded RNA viruses are selected from the group consisting of hepatitis C virus (HCV), Human Immunodeficiency virus (HIV) and Human T-cell Leukemia virus (HTLV).

8. The assay of claim 4 wherein the three different positive-stranded RNA viruses are hepatitis C virus (HCV), Human Immunodeficiency virus (HIV) and Human T-cell Leukemia virus (HTLV).

9. The assay of claim 1 or 2 wherein the assay is selected from the group consisting of a countercurrent immunoelectrophoresis (CIEP) assay, a radioimmunoassay, a western blot assay, a radioimmunoprecipitation, an enzyme-linked immuno-sorbent assay (ELISA), a dot blot assay, an inhibition or competition assay, a sandwich assay, an immunostick (dip-stick) assay, a simultaneous assay, an immunochromatographic assay, an immunofiltration assay, a latex bead agglutination assay, an immunofluorescent assay, a biosensor assay, and a low-light detection assay.

10. A composition comprising two or more different antigens capable of binding to an antibody against an HBcAg or an antibody against an independent core-like antigen of a positive stranded RNA virus, the composition comprising a) an isolated HBcAg complexed with a protein selected from the group consisting of a serum albumin and a core-like antigen-adjacent protein of a positive stranded RNA virus and b) an independent core-like antigen-adjacent protein of a positive stranded RNA virus complexed to a protein, to provide an isolated HBcAg-protein complex and an independent core-like antigen-adjacent protein complex.

11. The composition of claim 10 wherein the composition comprises at least two of the independent core-like antigen-adjacent proteins, at least two of which are from different positive-stranded RNA viruses.

12. The composition of claim 10 wherein the composition comprises at least three of the independent core-like antigen-adjacent proteins, at least three of which are from different positive-stranded RNA viruses.

13. The composition of any one of claims 10 to 12 wherein the positive stranded RNA virus is selected from the group consisting of Togaviridae, Coronaviridae, Retroviridae, Picornaviridae, Caliciviridae and Flaviviridae.

14. The composition of any one of claims 10 to 12 wherein the positive-stranded RNA virus is selected from the group consisting of hepatitis C virus (HCV), Human Immunodeficiency virus (HIV) and Human T-cell leukemia virus (HTLV).

15. The composition of claim 14 wherein the two different positive-stranded RNA viruses are selected from the group consisting of hepatitis C virus (HCV), Human Immunodeficiency virus (HIV) and Human T-cell Leukemia virus (HTLV).

16. The composition of claim 14 wherein the three positive-stranded RNA viruses are hepatitis C virus (HCV), Human Immunodeficiency virus (HIV) and Human T-cell Leukemia virus (HTLV).

17. The composition of any one of claims 10 to 12 wherein the core-like antigen-adjacent protein is produced by a suitable prokaryotic host cell.

18. The composition of any one of claims 10 to 12 wherein the core-like antigen-adjacent protein is produced by a eukaryotic host cell that is unable to process the core-like antigen-adjacent protein.

19. The composition of any one of claims 10 to 12 wherein the serum albumin is selected from the group consisting of human serum albumin, $\alpha$-fetoprotein, bovine serum albumin, fetal bovine serum albumin, new born bovine serum albumin and mouse serum albumin.

20. The composition of claim 19 wherein the serum albumin is human serum albumin.

21. A kit for the detection of an HBcAg, comprising:

(a) an HBcAg-protein complex comprised of the HBcAg complexed with a core-like antigen-adjacent protein of a positive stranded RNA virus; and (b) one or both of a reagent or a device for detecting an antibody bound to the complex.

22. The kit of claim 21 wherein the composition further comprises an independent core-like antigen of a positive stranded RNA virus complexed to a protein.

23. The kit of claim 22 wherein the composition further comprises at least two of the independent core-like antigen-adjacent proteins, at least two of which are from different positive-stranded RNA viruses.

24. The kit of claim 23 wherein the composition comprises at least three of the independent core-like antigen-adjacent proteins, at least three of which are from different positive-stranded RNA viruses.

* * * * *